(12) United States Patent
Wu et al.

(10) Patent No.: US 12,210,807 B2
(45) Date of Patent: Jan. 28, 2025

(54) MODELING METHOD AND APPARATUS FOR MODEL OF TRACING THE ORIGIN OF DURIANS, AND METHOD FOR TRACING THE ORIGIN OF DURIANS

(71) Applicant: FOOD INSPECTION AND QUARANTINE TECHNOLOGY CENTER OF SHENZHEN CUSTOMS DISTRICT, Guangdong (CN)

(72) Inventors: Hao Wu, Guangdong (CN); Baohui Jin, Guangdong (CN); Zhi Yan, Guangdong (CN); Xu Zhao, Guangdong (CN); Chengui Xiao, Guangdong (CN); Xiuwen Zhou, Guangdong (CN)

(73) Assignee: FOOD INSPECTION AND QUARANTINE TECHNOLOGY CENTER OF SHENZHEN CUSTOMS DISTRICT, Shenzhen (CN)

(*) Notice: Subject to any disclaimer, the term of this patent is extended or adjusted under 35 U.S.C. 154(b) by 877 days.

(21) Appl. No.: 17/417,915

(22) PCT Filed: Mar. 5, 2021

(86) PCT No.: PCT/CN2021/079210
§ 371 (c)(1),
(2) Date: Jun. 24, 2021

(87) PCT Pub. No.: WO2022/141793
PCT Pub. Date: Jul. 7, 2022

(65) Prior Publication Data
US 2023/0133180 A1 May 4, 2023

(30) Foreign Application Priority Data
Dec. 29, 2020 (CN) .......................... 202011599323.9

(51) Int. Cl.
*G06F 30/27* (2020.01)
*G06Q 30/018* (2023.01)
*G01N 33/02* (2006.01)

(52) U.S. Cl.
CPC ........... *G06F 30/27* (2020.01); *G06Q 30/018* (2013.01); *G01N 33/025* (2013.01)

(58) Field of Classification Search
CPC ...... G06F 30/27; G06Q 30/018; G06Q 50/02; G06Q 10/067; G01N 33/025; G01N 27/62
See application file for complete search history.

(56) References Cited

U.S. PATENT DOCUMENTS

2008/0032406 A1* 2/2008 Fry ....................... G01N 33/143
436/20
2009/0042304 A1* 2/2009 Anderson .............. G01N 33/02
436/20

FOREIGN PATENT DOCUMENTS

CN 108982692 A 12/2018
CN 111563752 A 8/2020

OTHER PUBLICATIONS

Mimmo, Tanja, et al. "Traceability of different apple varieties by multivariate analysis of isotope ratio mass spectrometry data." Rapid Communications in Mass Spectrometry 29.21 (2015): 1984-1990. (Year: 2015).*

Perez, Angela L., Brian W. Smith, and Kim A. Anderson. "Stable isotope and trace element profiling combined with classification models to differentiate geographic growing origin for three fruits: effects of subregion and variety." Journal of Agricultural and Food Chemistry 54.13 (2006): 4506-4516. (Year: 2006).*

(Continued)

*Primary Examiner* — Nithya J. Moll

(57) ABSTRACT

Provided is a modeling method and apparatus for a model of tracing the origin of durians, and a method for tracing the origin of durians. The modeling method includes obtaining isotope analysis data of pulp and seeds of durians of a target production area; generating a model of tracing the origin for (Continued)

a corresponding target production area through a preset analysis modeling algorithm using the isotope analysis data and information of the corresponding target production area; and validating an accuracy of the model of tracing the origin using the isotope analysis data of the target production area and other production areas, to obtain the accuracy of the model. The modeling method for a model of tracing the origin of durians of the present application performs isotope analysis on durians of the target production area, and generates a corresponding model of tracing the origin after obtaining isotope analysis data.

4 Claims, 3 Drawing Sheets

(56) References Cited

OTHER PUBLICATIONS

Striegel, Lisa, et al. "Durian fruits discovered as superior folate sources." Frontiers in Nutrition 5 (2018): 114.*
Ahmad, Izham, and P. C. Chua. "Trends in production and trade of tropical fruits in ASEAN countries." IV International Symposium on Tropical and Subtropical Fruits 975. 2008. (Year: 2008).*
Zhou, Xiuwen et al., Discrimination of Different Geographical Origins of Durian Based on Mineral Element Fingerprints Characteristics, Food Science, Nov. 23, 2020.
International Search Report of PCT Patent Application No. PCT/CN2021/079210 issued on Sep. 28, 2021.

* cited by examiner

MODELING METHOD AND APPARATUS FOR MODEL OF TRACING THE ORIGIN OF DURIANS, AND METHOD FOR TRACING THE ORIGIN OF DURIANS

CROSS REFERENCE TO RELATED APPLICATIONS

The present application is based on Chinese patent application No. 202011599323.9 filed on Dec. 29, 2020 and claims its priority. The entire disclosure of the application is hereby incorporated by reference in its entirety.

TECHNICAL FIELD

The present application relates to a modeling method and apparatus for a model of tracing the origin of durians, and a method for tracing the origin of durians, a computer equipment and readable storage medium.

BACKGROUND TECHNOLOGY

Generally, for the identification of the origin of imported durians, analysis of the compositions of durian samples and comparison of the compositions are conducted manually by the import and export inspection department, which is inefficient.

SUMMARY

In view of the above-mentioned problems, the present application provides a modeling method and apparatus for a model of tracing the origin of durians, and a method for tracing the origin of durians, a computer equipment and readable storage medium.

In order to achieve the above objectives, the present application provides the following technical proposals:

a modeling method for a model of tracing the origin of durians, including: obtaining isotope analysis data of pulp and seeds of durians of a target production area;

generating a model of tracing the origin for a corresponding target production area through a preset analysis modeling algorithm using the isotope analysis data and information of the corresponding target production area; and validating an accuracy of the model of tracing the origin using the isotope analysis data of the target production area and other production areas, to obtain the accuracy of the model.

Preferably, the modeling method for a model of tracing the origin of durians further includes:

performing leave-one-out cross validation on the accuracy using the model and isotope analysis data of a plurality of the target production areas, to validate corresponding accuracy of the plurality of the target production areas.

Preferably, in the modeling method for a model of tracing the origin of durians, the isotope analysis data include a $^2H$ isotope ratio, an $^{18}O$ isotope ratio, a $^{13}C$ isotope ratio, a $^{15}N$ isotope ratio, a $^{34}S$ isotope ratio, N content, S content and C content in a seed, as well as a $^2H$ isotope ratio, an $^{18}O$ isotope ratio, a $^{13}C$ isotope ratio, a $^{15}N$ isotope ratio, a $^{34}S$ isotope ratio, N content, S content and C content in the pulp.

Preferably, in the modeling method for a model of tracing the origin of durians, the preset analysis modeling algorithm includes at least one of stepwise discriminant analysis, linear discriminant analysis algorithm, and neural network algorithm.

Preferably, in the modeling method for a model of tracing the origin of durians, models of tracing the origin include models for Malaysia, Thailand, Cambodia and Vietnam.

Preferably, amongst the modeling method for a model of tracing the origin of durians, the model for Malaysia is, $Y_{Malaysia}=5.968X_1-37.228X_2-0.967X_3+3.898X_4+9.127X_5+14.190X_6+5.096X_7-815.054;$ the model for Thailand is, $Y_{Thailand}=4.315X_1-37.478X_2-1.225X_3+4.410X_4+11.772X_5+11.364X_6+3.659X_7-769.801;$ the model for Cambodia is, $Y_{Cambodia}=7.516X_1-40.351X_2-1.234X_3+4.699X_4+11.963X_5+14.355X_6+6.921X_7-921.633;$ the model for Vietnam is, $Y_{Vietnam}=5.607X_1-37.671X_2-1.092X_3+5.100X_4+18.562X_5+13.524X_6+5.601X_7-864.359;$ wherein, $X_1$ is the D isotope ratio in the seed, $X_2$ is the $^{13}C$ isotope ratio in the seed, $X_3$ is the D isotope ratio in the pulp, $X_4$ is the $^{18}O$ isotope ratio in the pulp, $X_5$ is the N content in the seed, $X_6$ is the C content in the seed, $X_7$ is the N content in the pulp, and Y is an output value.

The present application further provides a method for tracing the origin of durians, including:

obtaining isotope analysis data of pulp and a seed of a sample durian;

inputting the isotope analysis data into a plurality of models of tracing the origin established by the modeling method, and obtaining output values of the plurality of the models of tracing the origin; and determining the production area corresponding to the model with a highest output value as the origin of the sample durian.

The present application further provides a modeling apparatus for a model of tracing the origin of durians, including:

an analysis data acquiring module for acquiring isotope analysis data of pulp and seeds of durians from target production areas;

a model generating module for generating a model of tracing the origin for a target production area through a preset analysis modeling algorithm using the isotope analysis data and information of corresponding target production area; and an accuracy acquiring module for validating an accuracy of the model of tracing the origin using the isotope analysis data of the target production area and other production areas, to obtain the accuracy of the model.

The present application further provides a computer equipment including a memory and a processor, the memory stores a computer program, and the processor runs the computer program so that the computer equipment executes the modeling method for a model of tracing the origin of durians, and/or executes the method for tracing the origin of durians.

The present application further provides a readable storage medium, which stores a computer program that executes the modeling method for a model of tracing the origin of durians and/or the method for tracing the origin of durians, when the computer program runs on a processor.

The present application provides a modeling method for a model of tracing the origin of durians, which includes: obtaining isotope analysis data of pulp and seeds of durians of a target production area; generating a model of tracing the origin for a corresponding target production area through a preset analysis modeling algorithm using the isotope analysis data and information of the corresponding target production area; and validating an accuracy of the model of tracing the origin using the isotope analysis data of the target production area and other production areas, to obtain the accuracy of the model. The modeling method for a model of tracing the origin of durians of the present application performs isotope analysis on durians of the target production area, and generates a corresponding model of tracing the origin after obtaining isotope analysis data. The model of tracing the origin may quickly and accurately determine the production area of the durian sample, thereby improving the efficiency of inspection of the production area.

In order to make the above-mentioned objects, features and advantages of the present application more obvious and easier to understand, preferred embodiments are described in detail below in conjunction with the accompanying drawings.

BRIEF DESCRIPTION OF THE DRAWINGS

In order to more clearly illustrate the technical proposals of the present application, the drawings used in the embodiments will be briefly described below. It should be understood, the drawings in the following description are merely some embodiments of the present application, and shall not be considered as limitation to the scope of protection of the present application. In each drawing, similar components are numbered with similar reference signs.

DESCRIPTION OF THE EMBODIMENTS

Figure 1:
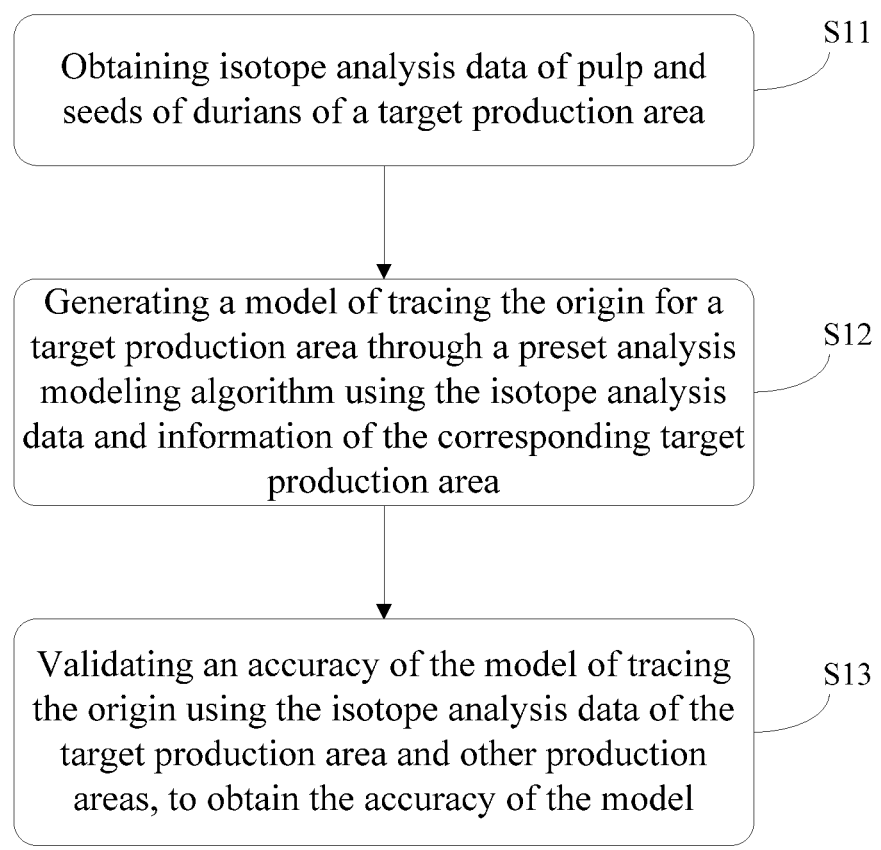
FIG. 1 is a flowchart of a modeling method for a model of tracing the origin of durians according to Embodiment 1 of the present application.

The technical proposals in the embodiments will be clearly and completely described below with reference to the accompanying drawings of the embodiments of the application. It is apparent that the embodiments to be described below are merely a part of the embodiments of the present application, and not all of them.

The components of the embodiments of the present application described and illustrated in the drawings herein may be arranged and designed in various different configurations. Therefore, the following detailed description of the embodiments of the present application shown in the accompanying drawings is not intended to limit the claimed scope of protection of the present application, but merely represents selected embodiments of the present application. All other embodiments obtained by those skilled in the art based on the embodiments of the present application without creative work shall fall within the scope of protection of the present application.

Hereinafter, when used in this specification and the appended claims, the terms "include" and "comprise" indicate the presence of the described features, integers, steps, operations, elements and/or components, but do not preclude the presence or addition of a plurality of other features, integers, steps, operations, elements, components, and/or collections thereof.

In addition, the terms "first", "second", "third", etc. are only used for distinguishing description, and cannot be understood as indicating or implying relative importance.

Unless otherwise indicated, all terms (including technical and scientific terms) used herein have the same meanings as commonly understood by those skilled in the art of which various embodiments of the present application belong. The terms (such as those defined in commonly used dictionaries) are to be interpreted as having the same meaning as those in the context of the relevant technical field and will not be interpreted as having an idealized meaning or an overly formal meaning, unless clearly defined in various embodiments of the present application.

Embodiment 1

FIG. 1 is a flowchart of a modeling method for a model of tracing the origin of durians according to Embodiment 1 of the present application. The modeling method includes:

Step S11: obtaining isotope analysis data of pulp and seeds of durians of a target production area.

In the embodiment of the present application, the isotope analysis data includes the isotope content of at least one element and the isotope ratio of at least one element in the pulp, and the isotope content of at least one element and the isotope ratio of at least one element in the seed. The element content includes the content of carbon, nitrogen, and sulfur, and the isotope ratio includes the stable isotope ratio of nitrogen, carbon, sulfur, hydrogen, and oxygen. Preferably, the isotope analysis data include a $^2$H isotope ratio, an $^{18}$O isotope ratio, a $^{13}$C isotope ratio, a $^{15}$N isotope ratio, a $^{34}$S isotope ratio, N content, S content and C content in a seed, as well as $^2$H isotope ratio, $^{18}$O isotope ratio, $^{13}$C isotope ratio, 15N isotope ratio, 34S isotope ratio, N content, S content and C content in the pulp.

In the embodiment of the present application, the above-mentioned isotope analysis data is directly obtained by chemical composition analysis on durians of the target production area. The detailed analysis process, for example, of a durian sample from Malaysia includes firstly taking out the pulp and seed of a fresh durian; after the seed is washed with fresh water, rinsing the core with ultrapure water (resistivity>18.2 M Ω·cm, 20° C.) and drying; washing the pulp with acetone for three times to remove sugar in the pulp, followed by washing with ultrapure water for another three times; drying the seed and pulp in an oven at 60° C. until a constant weight is reached; grinding the seed and pulp into powders with a ball mill (e.g. MM400 ball mill, Retsch, Germany); and sieving the powders for 80 times and storing in a dry environment. In order to carry out isotope and content determination of carbon, nitrogen, and sulfur of the above treated durian powder for analyzing the stable isotopes and content of carbon, nitrogen, and sulfur, a stable isotope ratio mass spectrometer (e.g. Delta V advantage, Thermo Fisher, Germany) with an element analyzer may be used. The stable isotope ratio analysis of hydrogen and oxygen can be carried out using a table isotope ratio mass spectrometer (e.g. Delta V Advantage, Thermo Fisher, Germany) and an elemental analyzer (HT2000) to determine the isotopes of hydrogen and oxygen. The above-mentioned instrument can be connected to a computer equipment through network communication, so that the computer equipment can directly read the isotope analysis data obtained by the instrument.

Step S12: generating a model of tracing the origin for a target production area through a preset analysis modeling algorithm using the isotope analysis data and information of the corresponding target production area.

In the embodiment of the present application, after the isotope analysis data is obtained by the computer equipment, a model of tracing the origin for a target production area is generated through a preset analysis modeling algorithm using the isotope analysis data and information of the corresponding target production area. The preset analysis modeling algorithm includes at least one of stepwise discriminant analysis, linear discriminant analysis algorithm, and neural network algorithm. For example, a model coefficient matrix, namely a model of tracing the origin, can be obtained after modeling through a linear discriminant algorithm.

In the embodiment of the present application, models of tracing the origin include models for Malaysia, Thailand, Cambodia and Vietnam. The model for Malaysia is, $$Y_{Malaysia} = 5.968X_1 - 37.228X_2 - 0.967X_3 + 3.898X_4 + 9.127X_5 + 14.190X_6 + 5.096X_7 - 815.054;$$

the model for Thailand is, $$Y_{Thailand} = 4.315X_1 - 37.478X_2 - 1.225X_3 + 4.410X_4 + 11.772X_5 + 11.364X_6 + 3.659X_7 - 769.801;$$

the model for Cambodia is, $$Y_{Cambodia} = 7.516X_1 - 40.351X_2 - 1.234X_3 + 4.699X_4 + 11.963X_5 + 14.355X_6 + 6.921X_7 - 921.633;$$

the model for Vietnam is, $$Y_{Vietnam} = 5.607X_1 - 37.671X_2 - 1.092X_3 + 5.100X_4 + 18.562X_5 + 13.524X_6 + 5.601X_7 - 864.359;$$

wherein, $X_1$ is the D (deuterium) isotope ratio in the seed, $X_2$ is the $^{13}C$ isotope ratio in the seed, $X_3$ is the D isotope ratio in the pulp, $X_4$ is the $^{18}O$ isotope ratio in the pulp, $X_5$ is the N content in the seed, $X_6$ is the C content in the seed, $X_7$ is the N content in the pulp, and Y is an output value. In practical applications, by more training samples, the coefficients of each model can be adjusted, thereby improving the accuracy of the discrimination of the model. When discriminating a sample from an unknown region, inputting $X_1$–$X_4$ of the sample from an unknown region into the above equations, and the region of the largest output value is determined to be the corresponding target production area.

Step S13: validating an accuracy of the model of tracing the origin using the isotope analysis data of the target production area and other production areas, to obtain the accuracy of the model.

In the embodiment of the present application, after a model of tracing the origin is generated, the isotope analysis data of multiple durian samples with known origins and the isotope analysis data of multiple corresponding target production areas may be used to calculate the number of correct identifications of the model to obtain the accuracy. According to whether the accuracy of the model of tracing the origin passes the minimum accuracy value, it is determined whether sample training is further required, thereby improving the accuracy of the model.

In the embodiment of the present application, isotope analysis on durian of the target production area is carried out to generate a corresponding model of tracing the origin. The model of tracing the origin may quickly and accurately identify the production area of a sample durian, thereby improving the efficiency of detection of the durian production area.

Embodiment 2

Figure 2:
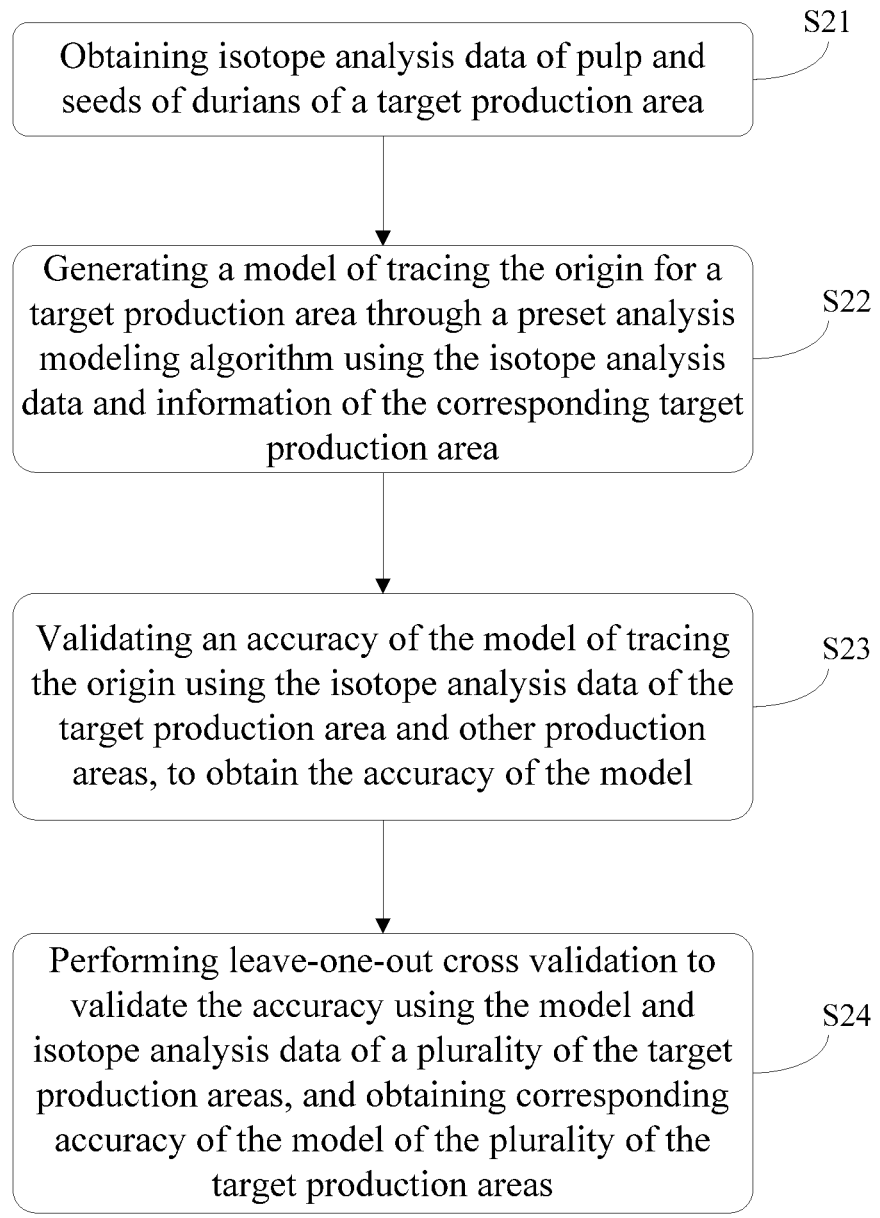
FIG. 2 is a flowchart of a modeling method for a model of tracing the origin of durians according to Embodiment 2 of the present application.

FIG. 2 is a flowchart of a modeling method for a model of tracing the origin of durians according to Embodiment 2 of the present application. The modeling method includes:

Step S21: obtaining isotope analysis data of pulp and seeds of durians of a target production area.

This step is the same as the above-mentioned step S11, hence will not be repeated here.

Step S22: generating a model of tracing the origin for a corresponding target production area through a preset analysis modeling algorithm using the isotope analysis data and information of the corresponding target production area.

This step is the same as the above-mentioned step S12, hence will not be repeated here.

Step S23: validating an accuracy of the model of tracing the origin using the isotope analysis data of the target production area and other production areas, to obtain the accuracy of the model.

This step is the same as the above-mentioned step S13, hence will not be repeated here.

Step S24: performing leave-one-out cross validation to validate the accuracy using the model and isotope analysis data of a plurality of the target production areas, and obtaining corresponding accuracy of the model of the plurality of the target production areas.

In the embodiment of the present application, the isotope analysis data can be retained after generating the model of the plurality of the target production areas, and can be used for performing leave-one-out cross validation to validate the accuracy of the model of tracing the origin of the plurality of the target production areas, thereby further enhancing the confidence in the accuracy of the model of tracing the origin.

Embodiment 3

Figure 3:
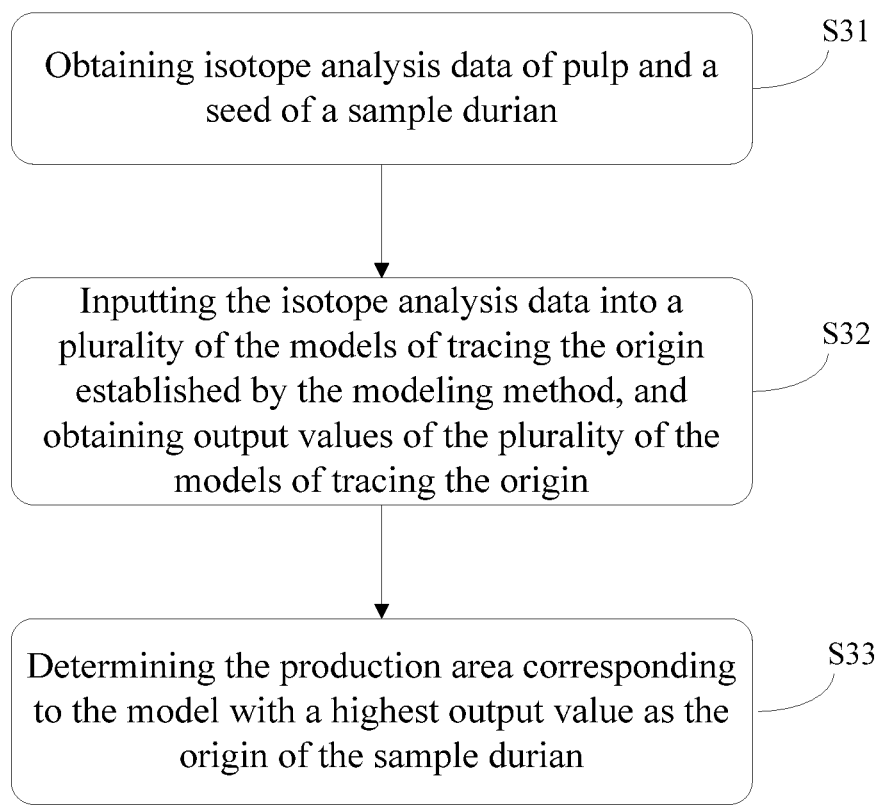
FIG. 3 is a flowchart of a method for tracing the origin of durians according to Embodiment 3 of the present application.

FIG. 3 is a flowchart of a method for tracing the origin of durians according to Embodiment 3 of the present application. The method includes:

Step S31: obtaining isotope analysis data of pulp and a seed of a sample durian.

Step S32: inputting the isotope analysis data into a plurality of the models of tracing the origin established by the modeling method, and obtaining output values of the plurality of the models of tracing the origin.

Step S33: determining the production area corresponding to the model with a highest output value as the origin of the sample durian.

Embodiment 4

Figure 4:
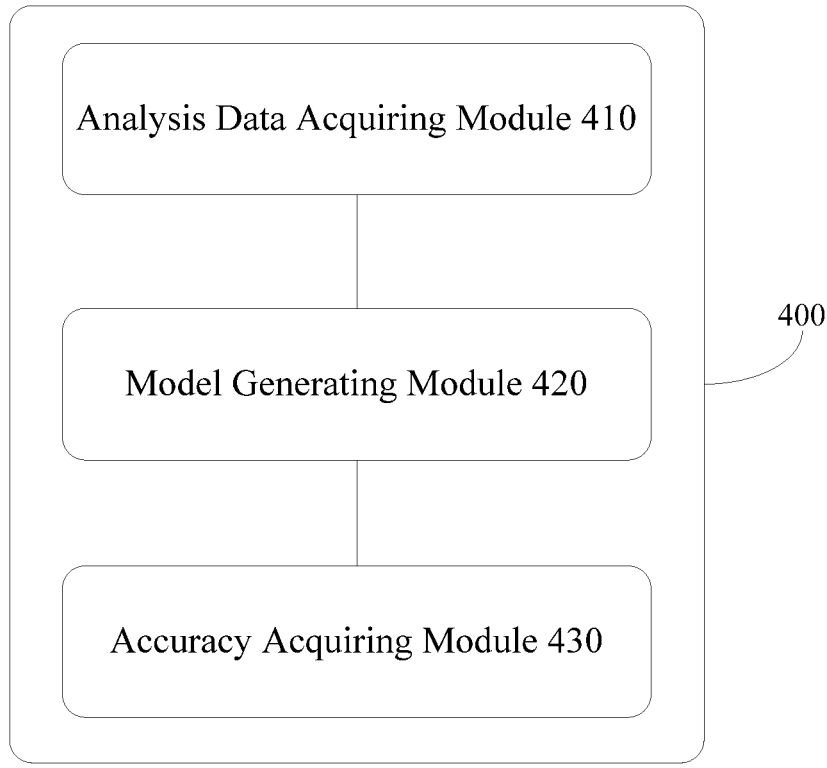
FIG. 4 is a structural diagram of a modeling apparatus for a model of tracing the origin of durians according to Embodiment 4 of the present application.

FIG. 4 is a structural diagram of a modeling apparatus for a model of tracing the origin of durians according to Embodiment 4 of the present application.

The modeling apparatus 400 includes:

an analysis data acquiring module 410 for acquiring the isotope analysis data of the pulp and the seed of the durians of the target production area;

a model generating module 420 for generating a model of tracing the origin for a target production area through a preset analysis modeling algorithm using the isotope analysis data and information of corresponding target production area; and an accuracy acquiring module 430 for validating an accuracy of the model of tracing the origin using the isotope analysis data of the target production area and other production areas, to obtain the accuracy of the model.

In the embodiment of the present application, the more detailed functional descriptions of the modules may be referred to the contents of the corresponding parts in the foregoing embodiments, which will not be repeated here.

In addition, the present application also provides a computer equipment that includes a memory and a processor. The memory can be used to store a computer program. The processor runs the computer program so that the computer equipment executes the above method or the function of each module in the modeling apparatus for a model of tracing the origin of durians.

The memory may include a program storage area and a data storage area. The program storage area may store an operating system, an application program required by at least one function (such as a sound playback function, an image playback function, etc.), and so on. The data storage area may store data (such as audio data, phone book, etc.) created according to the use of the computer equipment, etc. Furthermore, the memory may include a high-speed random access memory, and may also include a non-volatile memory, such as at least one magnetic disk storage device, a flash memory device, or other volatile solid-state storage devices.

The present embodiment further provides a readable storage medium for storing the computer program used in the above-mentioned computer equipment.

In the embodiments provided in the present application, it should be understood that the disclosed apparatus and method may also be implemented in other ways.

The apparatus embodiments described above are merely illustrative. For example, the flowcharts and structural diagrams in the accompanying drawings show the possible implementation architecture, functions and operations of the apparatus, methods, and computer program products according to multiple embodiments of the present application. In this regard, each block in the flowcharts or block diagrams may represent a module, program segment, or part of the code, and the module, program segment, or part of the code contains one or more executable instructions for realizing the specified logical function. It should also be noted that, in alternative implementations, the functions specified in the blocks may also take place in a different order from the order shown in the figures. For example, two consecutive blocks may actually be executed in parallel, or they may sometimes be executed in the reverse order, depending on the functions involved. It should also be noted that each block in the structural diagram and/or flowchart, and the combination of the blocks in the structural diagram and/or flowchart, can be implemented by a dedicated hardware-based system that performs specified functions or actions, or it can be implemented by a combination of dedicated hardware and computer instructions.

In addition, the functional modules or units in the various embodiments of the present application may be integrated together to form an independent part, or each module may exist alone, or two or more modules may be integrated to form an independent part.

If the aforementioned function is implemented in form of a software function module and sold or used as an independent product, it can be stored in a computer readable storage medium. Based on this understanding, the substantial technical proposal or the part that contributes to the existing technology or part of the technical proposal of the present application can be embodied in the form of a software product. The computer software product is stored in a storage medium and includes several instructions such that a computer equipment (which may be a smart phone, a personal computer, a server, or a network device, etc.) executes all or part of the steps of the methods described in the various embodiments of the present application. The aforementioned storage media include: USB disk, mobile hard disk, read-only memory (ROM), random access memory (RAM), magnetic disks or optical disks and other media that can store program codes.

The above are merely the detailed embodiments of the present application, but the scope of protection of the present application is not limited thereto. Any one skilled in the art can easily think of various equivalent modifications or substitutions within the technical scope disclosed in the present application. These modifications or substitutions shall fall within the scope of protection of the present application. Therefore, the scope of protection of the present application is defined by the appended claims.

What is claimed is:

1. An equipment for models of tracing an origin of a durian, comprising:
    a processor,
    a memory that is connected to the processor, wherein the memory stores a computer program for tracing the origin of the durian which is executed by the processor,
    a ball mill to grind a seed and pulp of the durian into powder;
    a stable isotope ratio mass spectrometer with an element analyzer is configured to determine isotope and content determination of carbon, nitrogen, and sulfur of the powder for analyzing stable isotopes and content of carbon, nitrogen, and sulfur;
    a stable isotope ratio to determine isotopes of hydrogen and oxygen of the powder;
    by the processor, obtaining isotope analysis data of the seed and pulp of the durian of target production areas;
    by the processor, generating the models of tracing the origin for the target production areas through preset analysis modeling algorithms using the isotope analysis data and information of the target production areas; and
    by the processor, validating accuracies of the models of tracing the origin using the isotope analysis data of the target production areas and other production areas, to obtain the accuracies of the models,
    wherein the isotope analysis data include a 2H isotope ratio, an 18O isotope ratio, a 13C isotope ratio, a 15N isotope ratio, a 34S isotope ratio, N content, S content, and C content in the seed, as well as a 2H isotope ratio, an 18O isotope ratio, a 3C isotope ratio, a 15N isotope ratio, a 34S isotope ratio, N content, S content and C content in the pulp.

2. The equipment for models of tracing the origin of the durian according to claim 1, further comprising:
    by the processor, performing leave-one-out cross validation on the accuracies using the models and isotope analysis data of the target production areas, to validate accuracies of the target production areas.

3. The equipment for models of tracing the origin of the durian according to claim 1, wherein the preset analysis modeling algorithms include at least one of a stepwise discriminant analysis, a linear discriminant analysis algorithm, and a neural network algorithm.

4. The equipment for models of tracing the origin of the durian according to claim 3, wherein a model for Malaysia is:

$$Y_{Malaysia}=5.968X_1-37.228X_2-0.967X_3+3.898X_4+9.127X_5+14.190X_6+5.096X_7-815.054;$$

wherein a model for Thailand is:

$$Y_{Thailand}=4.315X_1-37.47X_2-1.225X_3+4.410X_4+11.772X_5+11.364X_6+3.659X_7-769.801;$$

wherein a model for Cambodia is:

$$Y_{Cambodia}=7.516X_1-40.351X_2-1.234X_3+4.699X_4+11.963X_5+14.355X_6+6.921X_7-921.633;$$

wherein a model for Vietnam is:

$$Y_{Vietnam}=5.607X_1-37.671X_2-1.092X_3+5.100X_4+18.562X_5+13.524X_6+5.601X_7-864.359;$$

wherein, $X_1$ is the deuterium (D) isotope ratio in the seed, $X_2$ is the 13C isotope ratio in the seed, $X_3$ is the D isotope ratio in the pulp, $X_4$ is the 18O isotope ratio in the pulp, $X_5$ is the N content in the seed, $X_6$ is the C content in the seed, $X_7$ is the N content in the pulp, and Y is an output value.

* * * * *